(12) United States Patent
Liu

(10) Patent No.: US 10,330,675 B2
(45) Date of Patent: Jun. 25, 2019

(54) IMMUNOBLOTTING SYSTEMS AND METHODS

(71) Applicant: Bio-Rad Laboratories, Inc., Hercules, CA (US)

(72) Inventor: Ning Liu, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 407 days.

(21) Appl. No.: 15/003,536

(22) Filed: Jan. 21, 2016

(65) Prior Publication Data

US 2016/0216255 A1  Jul. 28, 2016

Related U.S. Application Data

(60) Provisional application No. 62/107,131, filed on Jan. 23, 2015.

(51) Int. Cl.
*G01N 33/543* (2006.01)

(52) U.S. Cl.
CPC .............................. *G01N 33/54306* (2013.01)

(58) Field of Classification Search
None
See application file for complete search history.

(56) References Cited

U.S. PATENT DOCUMENTS

| | | |
|---|---|---|
| 6,326,058 B1 | 12/2001 | Biebuyck et al. |
| 7,329,111 B2 | 2/2008 | Delamarche et al. |
| 7,371,684 B2 | 5/2008 | Colburn et al. |
| 7,491,272 B2 | 2/2009 | Delamarche et al. |
| 7,695,687 B2 | 4/2010 | Delamarche et al. |
| 7,740,472 B2 | 6/2010 | Delamarche et al. |
| 7,855,101 B2 | 12/2010 | Furman et al. |
| 7,947,907 B2 | 5/2011 | Colburn et al. |
| 7,980,446 B2 | 7/2011 | Buchwalter et al. |
| 7,982,312 B2 | 7/2011 | Colburn et al. |
| 7,992,591 B2 | 8/2011 | Delamarche |
| 8,020,586 B2 | 9/2011 | Delamarche |
| 8,051,878 B2 | 11/2011 | Delamarche |
| 8,206,025 B2 | 6/2012 | Natarajan |
| 8,491,083 B2 | 7/2013 | Boday et al. |
| 8,517,596 B2 | 8/2013 | Natarajan |
| 8,551,859 B2 | 10/2013 | Ackerson et al. |
| 8,585,280 B2 | 11/2013 | Natarajan |
| 8,674,474 B2 | 3/2014 | Ackerson et al. |

(Continued)

FOREIGN PATENT DOCUMENTS

| | | |
|---|---|---|
| WO | 2012/166041 A1 | 12/2012 |
| WO | 2014/165185 A1 | 10/2014 |

OTHER PUBLICATIONS

International Search Report and Written Opinion dated May 12, 2016 in PCT/US16/14337, 13 pages.

(Continued)

*Primary Examiner* — Rebecca L Martinez
(74) *Attorney, Agent, or Firm* — Kilpatrick Townsend and Stockton LLP

(57) ABSTRACT

Immunoblotting systems and method are provided. In one embodiment, the method may be achieved by applying an antibody solution to a surface of a membrane having an optically detectable protein and a target protein transferred thereon, wherein the application of the antibody solution is guided by a signal emitted from the optically detectable protein; and detecting the target protein. Systems and other methods are also described and illustrated.

18 Claims, 9 Drawing Sheets

(56) References Cited

U.S. PATENT DOCUMENTS

| | | |
|---|---|---|
| 8,680,023 B2 | 3/2014 | Coyer et al. |
| 8,680,024 B2 | 3/2014 | Coyer et al. |
| 8,695,639 B2 | 4/2014 | Delamarche et al. |
| 8,695,641 B2 | 4/2014 | Delamarche et al. |
| 2005/0069462 A1 | 3/2005 | Humenik et al. |
| 2005/0069949 A1 | 3/2005 | Humenik et al. |
| 2005/0247673 A1 | 11/2005 | Delamarche et al. |
| 2007/0134747 A1 | 6/2007 | DiGiammarino et al. |
| 2007/0231458 A1 | 10/2007 | Gale et al. |
| 2009/0318302 A1 | 12/2009 | Delamarche et al. |
| 2009/0318303 A1 | 12/2009 | Delamarche et al. |
| 2010/0176089 A1 | 7/2010 | Delamarche et al. |
| 2011/0117539 A1 | 5/2011 | Delamarche et al. |
| 2012/0034677 A1 | 2/2012 | Delamarche et al. |
| 2012/0214153 A1 | 8/2012 | Delamarche et al. |
| 2012/0283133 A1 | 11/2012 | Delamarche et al. |
| 2013/0098481 A1 | 4/2013 | Delamarche et al. |
| 2013/0121893 A1 | 5/2013 | Delamarche et al. |
| 2013/0333761 A1 | 12/2013 | Delamarche et al. |
| 2013/0337578 A1 | 12/2013 | Delamarche et al. |
| 2014/0004264 A1 | 1/2014 | Duerig et al. |
| 2014/0024024 A1 | 1/2014 | Sood et al. |
| 2014/0072777 A1 | 3/2014 | Boday et al. |
| 2014/0090715 A1 | 4/2014 | Delamarche et al. |
| 2014/0137962 A1 | 5/2014 | Delamarche et al. |
| 2014/0311909 A1 | 10/2014 | Siino, Jr. et al. |

OTHER PUBLICATIONS

Extended European Search Report for EP Application 16740765.9 dated May 11, 2018; 5 pages.

Ladner, C. et al.; "Visible Fluorescent detection of proteins in polyacrylamide gels without staining"; *Analytical Biochemistry*; vol. 326, No. 1; Mar. 1, 2004; pp. 13-20.

Short R. et al.; "Stain-Free Approach for Western Blotting; Alternative to the Standard Blot Normalization Process"; *Genetic Engineering & Biotechnology News.*; vol. 31, No. 20; Nov. 15, 2011; 3 pages.

Posch, A. et al.; "V3 Stain-Free Workflow for a Practical, Convenient, and Reliable Total Protein Loading Control in Western Blotting"; *Journal of Visualized Experiments*; No. 82; Dec. 30, 2013; 9 pages.

IMMUNOBLOTTING SYSTEMS AND METHODS

CROSS-REFERENCES TO RELATED APPLICATIONS

This application claims priority to U.S. Provisional Application No. 62/107,131, filed Jan. 23, 2015, which is incorporated by reference herein in its entirety for all purposes.

BACKGROUND OF THE INVENTION

Blotting is a process used to transfer macromolecules from an electrophoresis matrix to a membrane for further analysis. Southern blotting is used for DNA analysis, Northern blotting is used for RNA analysis and Western blotting is used for protein analysis.

In Western blotting (or immunoblotting), proteins in a sample are separated by sodium dodecyl sulfate-polyacrylamide gel electrophoresis (SDS-PAGE) and then transferred onto a membrane (e.g., nitrocellulose or polyvinylidene) by capillary action or electroblotting. After the proteins are immobilized on the surface of the membrane, the proteins are contacted with a primary antibody that specifically binds to a target protein. The bound primary antibody is then detected, for example, by contacting the primary antibody with a secondary antibody conjugated to a detectable label such as a fluorescent label. The detectable label is then visualized by optical techniques (i.e., techniques that measure emitted light).

Although immunoblotting provides useful information, the technique is time consuming, requires a high level of technical skill, is reagent intensive, has limited throughput, and is poorly suited for multiplexing.

BRIEF SUMMARY OF THE INVENTION

Disclosed herein are immunoblotting systems and methods of using such systems.

In an embodiment, a method of immunoblotting comprises applying an antibody solution to a surface of a membrane having an optically detectable protein and a target protein transferred thereon, wherein the application of the antibody solution is guided by a signal emitted from the optically detectable protein; and detecting the target protein.

In some embodiments, the method further includes a washing step in which unbound material is removed from the membrane. In some embodiments, the antibody solution application step is concurrent with the washing step. In some embodiments, a microfluidic or sub-microfluidic volume of the antibody solution is dispensed onto the surface of the membrane. Application of the antibody solution may be performed with a technique selected from a group consisting of hydrodynamic flow confinement, ink jet printing, spray deposition, microspotting and microcontact printing. In some embodiments, the antibody solution is dispensed with a microfluidic probe. In an embodiment, the microfluidic probe has multiple microchannels. In another embodiment, the microfluidic probe is an array of probes.

In some embodiments, the antibody solution is dispensed in at least one discreet path on the surface of the membrane. In an embodiment, the path spans the length of one or more lanes of protein bands. In some embodiments, the path is from 25 nanometers to 500 micrometers wide. In certain embodiments, the antibody solution is dispensed in at least one discreet spot. In some embodiments, the applying an antibody solution step comprises dispensing a primary antibody solution and a secondary antibody solution. In some embodiments, the optically labeled protein transferred onto the membrane is labeled with a substance selected from the group consisting of a fluorescent dye, a colorimetric dye and haloalkane. In an embodiment, the method further comprises applying a blocking solution to the surface of the membrane prior to applying the antibody solution.

In some embodiments, a system for immunoblotting includes a membrane having an optically detectable protein transferred thereon; a dispenser configured to dispense an antibody solution; a light source configured to illuminate the membrane; a detector configured to detect the optically detectable protein; a processor; and a memory comprising a data storage unit for storing instructions that are executable by the processor and that configure the system to dispense the antibody solution in accordance with the optically detectable protein detected by the detector. In some embodiments, the detector is further configured to detect a target protein. In some embodiments, the system further includes a second detector configured to detect a target protein.

In other embodiments, configurations can be used to probe nucleic acid blots.

BRIEF DESCRIPTION OF THE DRAWINGS

FIG. 9A shows the path of the microfluidic probe superimposed on a photo of the blot prior to application of a primary antibody. The application of a primary antibody (e.g., anti-hSA) by the microfluidic probe to the hSA band was guided by prestained molecular weight markers in the lane adjacent to the lane containing hSA. FIG. 9B shows an image of the blot after application of the anti-hSA to the hSA band. FIG. 9C is a signal intensity profile across the path of the microfluidic probe.

FIG. 10A shows the path of the microfluidic probe superimposed on an image of the blot after application of anti-hSA. The application of anti-hSA by the microfluidic probe to the hSA band was guided by prestained molecular weight markers in the same lane as the hSA. FIG. 10B is a signal intensity profile across the path of the microfluidic probe.

DEFINITIONS

The term "optically detectable protein" refers to a protein labeled with a luminescent (e.g., fluorescent, colorimetric, phosphorescent or chemiluminescent) substance that, when irradiated with light, emits an optical signal.

DETAILED DESCRIPTION OF THE INVENTION

Described herein are systems and methods for immunoblotting. The systems and methods facilitate the automation of immunoblotting. An automated high throughput system and method of immunoblotting has been discovered that can test multiple samples at once, uses lower amounts of reagents, and can provide quick test results.

Advantages of the system and methods described herein include, but are not limited to: (1) providing systems that are automated or are "hands-free"; (2) providing systems that localize the reaction chemistry and decrease reaction time; (3) providing systems capable of performing multiplex tests (e.g., testing multiple protein samples at once or testing a single protein sample for multiple target proteins); (4) providing systems capable of real time detection of target proteins; (5) providing systems capable of depositing a smaller volume of reagent (e.g., antibody solution); (6) providing systems capable of using optically detectable proteins transferred onto the surface of a membrane to guide the application of an antibody solution onto the surface of the membrane, and/or (7) providing systems in which the application of an antibody solution and removal of unbound antibody may be performed simultaneously.

As used in this specification and the appended claims, the singular forms "a", "an", and "the" include plural referents unless the content clearly dictates otherwise. Thus, for example, reference to a system comprising "an antibody solution" includes systems comprising one or more antibody solutions. Likewise, reference to "an optically detectable protein" includes one or more optically detectable proteins.

Systems

Figure 1:
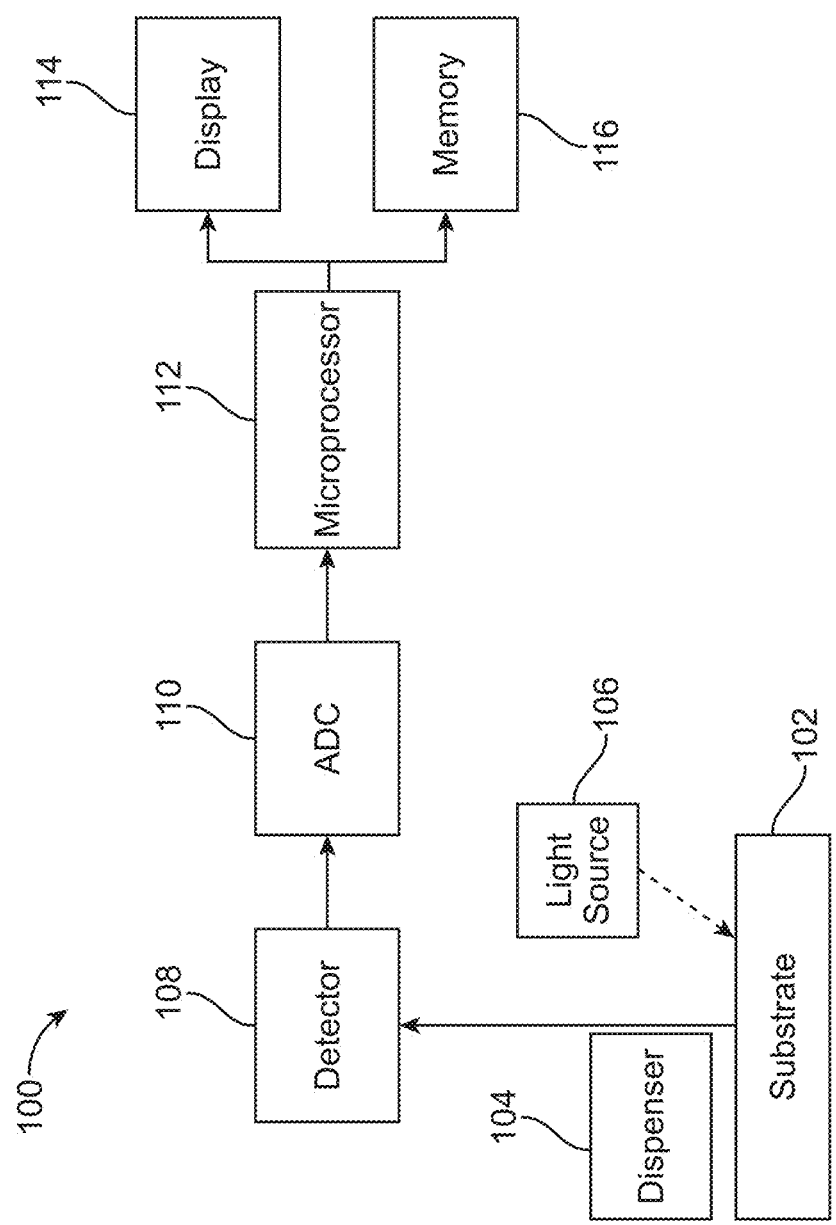
FIG. 1 shows a schematic view of an immunoblotting system according to an embodiment of the invention.

Referring to FIG. 1, a system 100 for immunoblotting is illustrated. In an embodiment, the system 100 is used to apply an antibody solution to an immunoblotting membrane to which an optically detectable protein and a target protein are transferred. The system 100 includes a membrane 102, a dispenser 104, a light source 106 and a detector 108.

Figure 2:
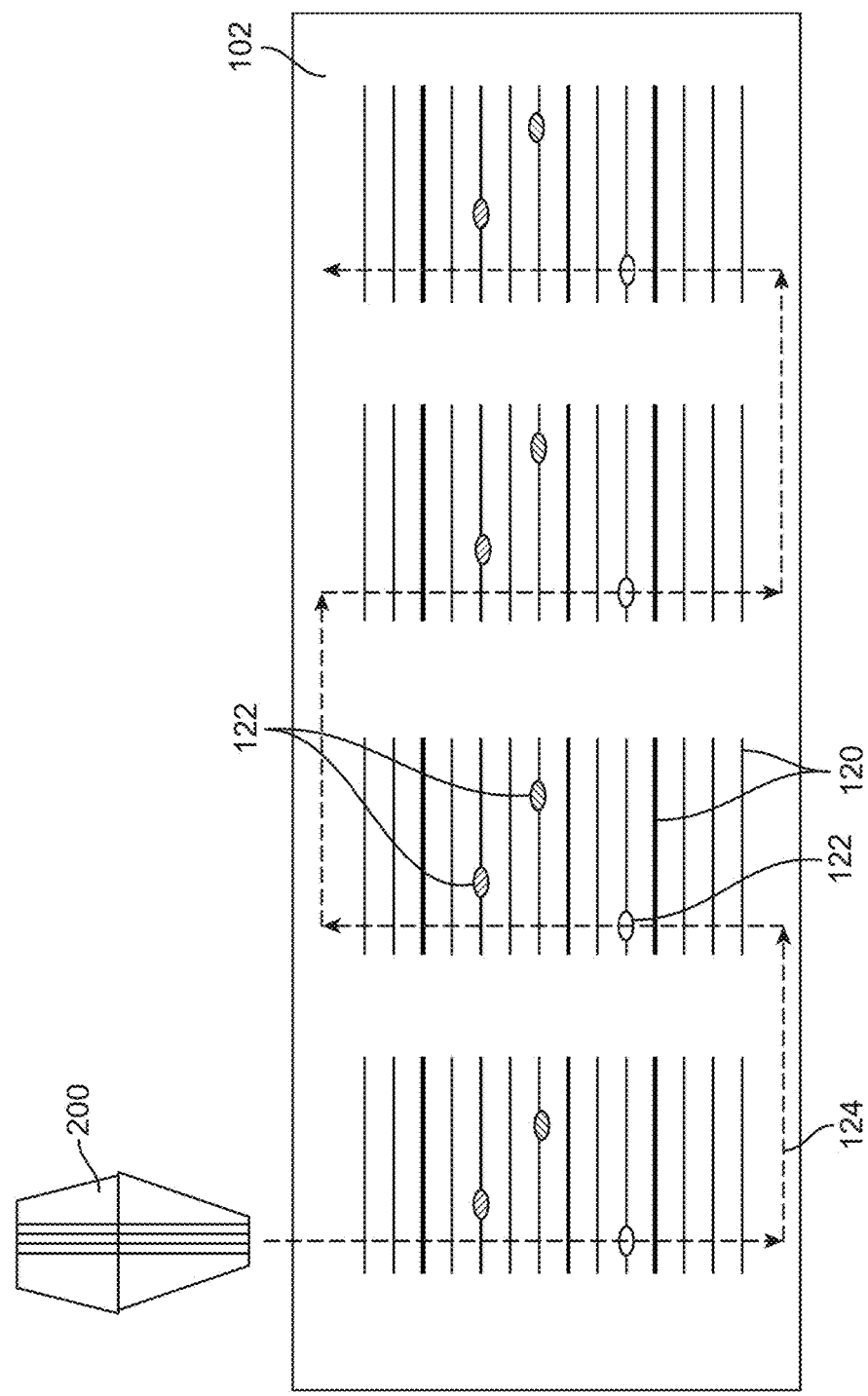
FIG. 2 shows a top view of a membrane having optically detectable proteins and target proteins transferred thereon in which an antibody solution is applied with a microfluidic probe according to an embodiment of the invention.

As illustrated in FIG. 2, the membrane 102 includes one or more optically detectable proteins 120 and target proteins 122 transferred from a polyacrylamide electrophoresis gel. In some embodiments, the membrane 102 is mounted on a platform that is moveable in the X-Y- and/or Z direction. In some embodiments, the membrane 102 is wet. A wet or moist membrane is desired to reduce background during detection of target proteins 122. Exemplary fluids used to hydrate the membrane 102 include, but are not limited to, buffer, blocking solution, water, and/or saline. Exemplary membrane materials include polyvinylidene difluoride, nylon, polysulfone and nitrocellulose.

In some embodiments, the optically detectable proteins 120 may be proteins labeled with a fluorescent dye, a colorimetric stain or a haloalkane (i.e., a halo-substituted organic compound). Some embodiments use haloalkanes as described in U.S. Pat. No. 8,007,646, which is incorporated by reference in its entirely. Exemplary fluorescent dyes include, but are not limited to, epicocconone, 2-methoxy-2, 4-diphenyl-3(2H)-furanon, ruthenium-based dyes (e.g., SYPRO® Ruby Protein Gel Stain), cyanine-based dyes, coumarin-based cyanine dyes (e.g., Bio-Rad Flamingo™) and Bio-Rad Oriole™. Exemplary colorimetric stains include COOMASSIE Brilliant Blue and silver nitrate. In some embodiments, the optically detectable proteins 120 are labeled before or during SDS-PAGE. In other embodiments, the optically detectable proteins 120 are labeled after they are transferred onto the blotting membrane 102. In an embodiment, haloalkane is included in the polyacrylamide gel and, upon exposure to UV light, the haloalkane covalently bonds with tryptophan residues in the proteins during SDS-PAGE. The resulting "stain-free" haloalkylated tryptophan-containing proteins may then be transferred to a membrane for immunostaining.

The target protein 122 may be any protein of interest. The target proteins 122 may include whole classes of proteins, e.g., enzymes, hormones, and/or antibodies.

Referring again to FIG. 1, the dispenser 104 is configured to dispense a microfluidic or sub-microfluidic volume of one or more antibody solutions each in a discreet path 124 on the surface of the membrane 102. In some embodiments, the path spans the length of one or more lanes of protein bands on the surface of the membrane 102. In an embodiment, the width of the path is from about 25 nanometers to about 500 micrometers wide. In certain embodiments, the width of the path is from about 25 micrometers to about 200 micrometers wide. In some embodiments, the path is continuous. In some embodiments, the path is discontinuous. In some embodiments, 1-50 antibody solutions are dispensed in parallel paths on a lane of protein bands. In other embodiments, 1-20 antibody solutions are dispensed in parallel paths on a lane of protein bands. In some embodiments, 1-10 antibody solutions are dispensed in parallel paths on a lane of protein bands. In some embodiments, one or more antibody solutions are dispensed in a pattern of spots and/or dots. In an embodiment, the spots/dots are about 25 nanometers to about 500 micrometers in diameter. In certain embodiments, the spots/dots are about 25 nanometers to about 200 micrometers in diameter. In an embodiment, an array of spots and/or dots covers a surface of the substrate.

In some embodiments, the dispenser 104 is moveable in the X-Y- and/or Z direction. Movement and functions of the dispenser 104 may be computer controlled.

Exemplary dispensers include a hydrodynamic flow confinement dispenser, an ink jet printer, a spray deposition dispenser, a microspotter and/or a microcontact printer. In an embodiment, the dispenser 104 is a microfluidic probe 200 that deposits one or more antibody solutions (e.g., primary and/or secondary antibody solutions) on the surface of the membrane 102. In an embodiment, the hydrodynamic flow confinement dispenser is a microfluidic probe (or vertical MFP) as described in U.S. patent application Ser. No. 13/881,989, which is incorporated by reference in its entirety herein. In an embodiment illustrated in FIGS. 3A and 3B, the microfluidic probe 200 may include a base layer 220, wherein processing liquid microchannels 223, 224 are provided together with immersion liquid microchannels 323, 324. Each channel is in fluid communication with an aperture 221, 222, 321, 322, each aperture located on a face of the base layer (not necessarily the same face), and preferably in close proximity. The channels 223, 224, 323, 324 also provide connection between motorized pumps and the apertures 221, 222, 321, 322. When moving the microfluidic probe 200 in the vicinity of a surface, processing liquid provided through the aperture 221 will combine with the immersion liquid and preferably inserts into immersion liquid provided via the apertures 321 and 322, as symbolized by the curved (thick) arrows of FIG. 3B. The latter are provided for the sake of understanding; their dimension are deliberately exaggerated. In this regard, in some embodiments, the device is configured such as to obtain a laminar flow. In some embodiments, the aperture dimensions may be tens of micrometers (e.g., 10-50 micrometers). In some embodiments, an aperture dimension may be 1-50 micrometers. The apertures are typically spaced apart by hundreds of micrometers (e.g., 200-500 micrometers). As pairs of processing channels/apertures are used herein, the processing liquid can be re-aspirated at aperture 222 together with some of the immersion liquid. Note that the flow path between apertures 221 and 222 can be inverted, i.e. processing liquid can be injected from aperture 222 while aperture 221 can aspirate liquid. The processing liquid can be essentially located nearby the apertures 221 and 222 and is surrounded by an immersion liquid that is essentially present in the vicinity of the head 200. A cover layer 210 closes the channels open on the upper face of the base layer, as depicted.

In addition, in some embodiments, portions of the processing liquid microchannels are provided as grooves 223', 224' in the layer thickness of the base layer 220, open on the upper face thereof. This way, forming a microchannel is easily achieved, in spite of its transverse dimensions (likely small, e.g., a few tens of micrometers). After assembly, the groove is closed by a portion of the cover layer 210. The groove may be engraved by a tool directly on the upper surface of the base layer 220. It can have any appropriate section shape, e.g. rounded, square, U or V section. The tool can be chosen according to the material of the base layer 220. In a variant, laser ablation can be contemplated. Most advantageously yet, deep reactive ion etching (DRIE) is used for fabrication of microchannels.

Figure 3B:
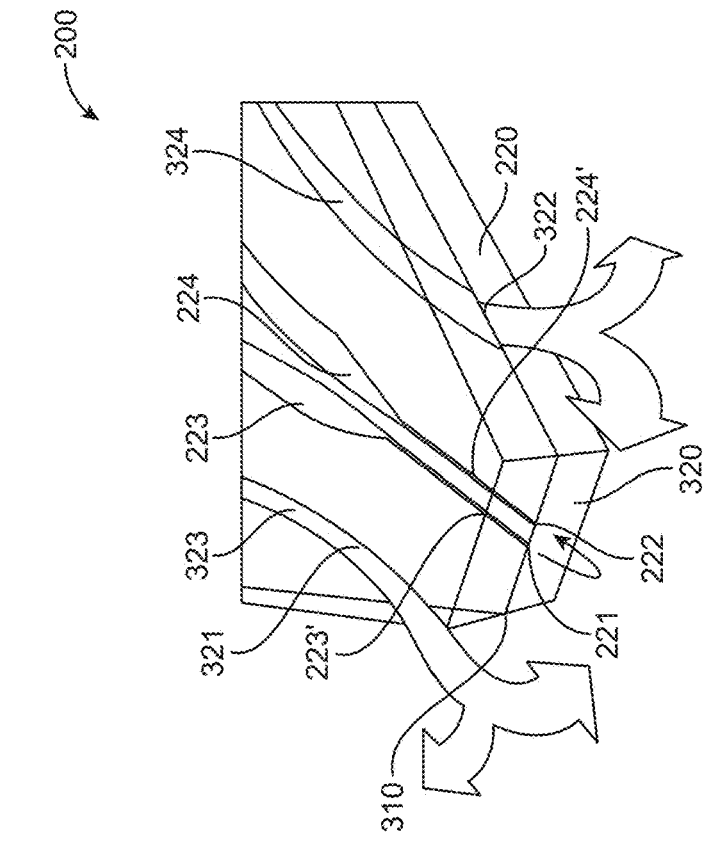
FIGS. 3A and 3B shows a microfluidic probe of the prior art.

As depicted in FIG. 3B, the grooves 223', 224' extend up to respective apertures 221, 222. Similarly, immersion channels 223, 224 reach respective apertures 321, 324. In this example, channels and apertures are symmetrically arranged around the main axis of the upper face of the head. An aperture is directly formed at an end of the groove at the level of an edge 310 of the front face 320 of the base layer 220, which here again is easily machined. Said front end 320 is typically made acute, which allows for compact liquid deposition on a surface of interest, and leaves rooms for easy optical monitoring.

Figure 3A:
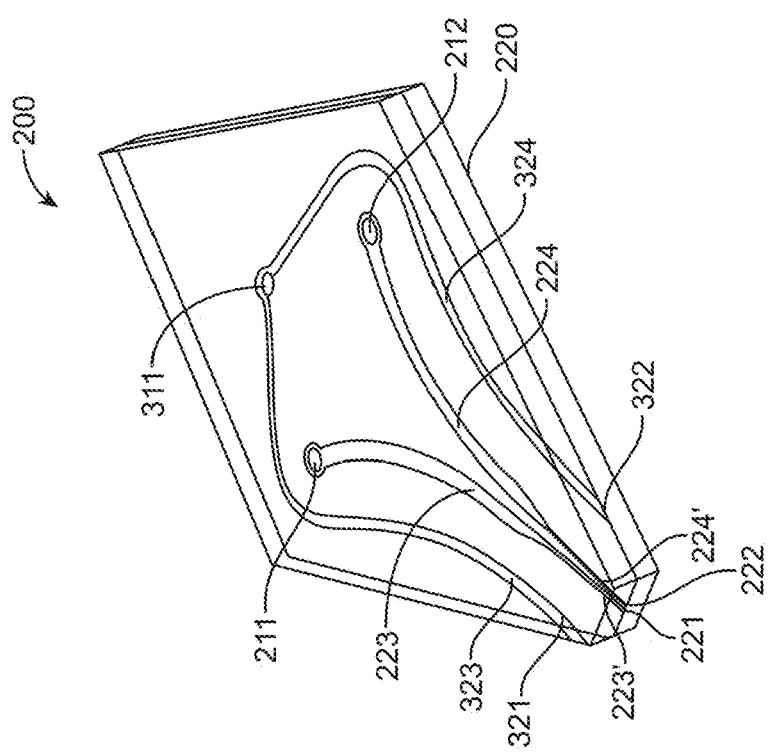

Referring to FIG. 3A, vias 211, 212 are provided on the cover layer 210. An additional via 311 is shown, which allows for relaying fluid communication to immersion channels 323, 324 (only one via is provided here, which feeds both immersion channels). Corresponding tubing ports connected to the vias can be provided (not shown). The channels have ends arranged such as to face the vias.

Figure 4:
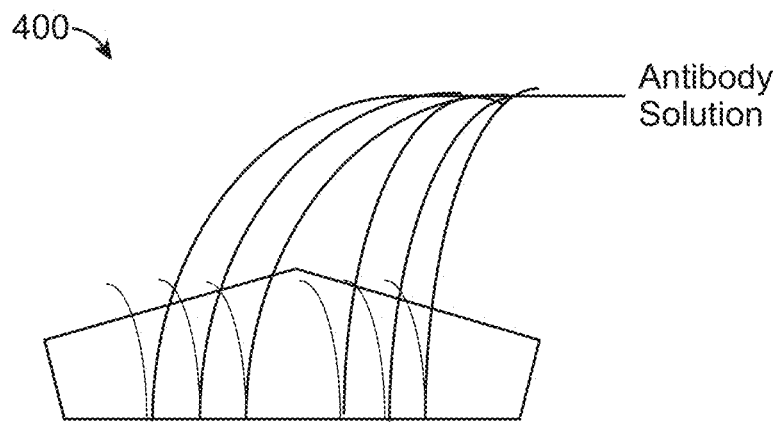
FIG. 4 shows a microfluidic probe having a plurality of processing liquid microchannels which may be connected to a single antibody solution or multiple antibody solutions according to an embodiment of the invention.

As depicted in FIGS. 3A and 3B, the microfluidic probe 200 includes two processing liquid microchannels. In some embodiments, the microfluidic probe 200 includes more than two processing liquid microchannels. In some embodiments, a microfluidic probe 400 includes 2-50 processing liquid microchannels (see FIG. 4). In some embodiments, the microfluidic probe 200 may include a heating element in at least one of the processing liquid microchannels. Heating the sample may increase the speed at which the antigens and antibodies react which may reduce test time.

Figure 5:
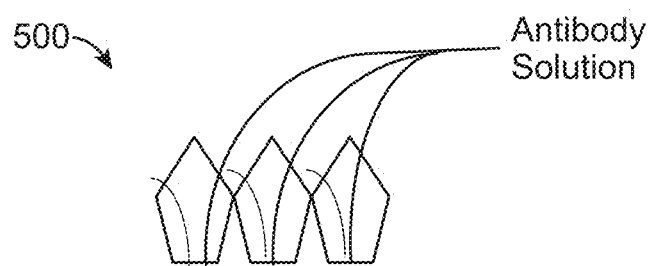
FIG. 5 shows multiple microfluidic probes in parallel connected to a single or multiple antibody solutions according to an embodiment of the invention.

In an embodiment illustrated in FIG. 5, the microfluidic probe is an array of probes connected in parallel (i.e., probe array 500) which may be connected to the same or different processing liquids. In another embodiment, each of the probes in the probe array 500 includes a plurality of microchannels.

Microfluidic probes may be formed of material that is compatible with the fluids flowing through the channels. Exemplary compatible materials include, but are not limited to, silicon, silica, polydimethylsiloxane (PDMS), gallium arsenide, glass, ceramics, quartz, polymers such as neoprene, Teflon™, polyethylene elastomers, polybutadiene/SBR, nitrites, nylon, and/or metals. The inner surface of the channels may also be coated with suitable material to reduce the affinity between the fluid components and the channels themselves.

Exemplary processing liquids include antibody solutions, buffer, blocking solution, oil (e.g., mineral oil) and/or air. Exemplary immersion liquids include buffer, blocking solution, and oil.

The processing and immersion liquids are configured to fill the microchannels in an efficient and reproducible manner. As such, the liquids are formulated to have an appropriate viscosity, hydrophilicity or hydrophobicity. In some embodiments, the liquids may include one or more surfactants, detergents, emulsifiers, solubilizers, to provide acceptable/optimal filling of the microchannels in a fast and reproducible manner. In some embodiments, the liquids comprise one or more of: ammonium lauryl sulfate, sodium lauryl sulfate (SDS, sodium dodecyl sulfate), sodium laureth sulfate, sodium myreth sulfate, dioctyl sodium sulfosuccinate, perfluorooctanesulfonate (PFOS), perfluorobutanesulfonate, linear alkylbenzene sulfonates (LABs), sodium stearate, sodium lauroyl sarcosinate, perfluorononanoate, perfluorooctanoate, alkyltrimethylammonium salts (e.g., cetyl trimethylammonium bromide), cetylpyridinium chloride (CPC), benzalkonium chloride (BAC), benzethonium chloride (BZT), 5-Bromo-5-nitro-1,3-dioxane, dimethyldioctadecylammonium chloride, cetrimonium bromide, dioctadecyldimethylammonium bromide (DODAB), CHAPS, cocamidopropyl hydroxysultaine, lecithin, polyoxyethylene glycol alkyl ethers, polyoxypropylene glycol alkyl ethers, glucoside alkyl ethers, polyoxyethylene glycol octylphenol ethers (e.g., Triton X-100), Polyoxyethylene glycol alkylphenol ethers, glycerol alkyl esters, polyoxyethylene glycol sorbitan alkyl esters (e.g., Polysorbate), sorbitan alkyl esters, cocamide MEA, cocamide DEA, dodecyldimethylamine oxide, block copolymers of polyethylene glycol and polypropylene glycol and/or polyethoxylated tallow amine (POEA).

In some embodiments, the liquids comprise tailored concentrations of Tween (e.g., Tween-20) and bovine serum albumin (BSA). In some embodiments, concentrations of Tween (e.g., Tween-20) and BSA are designed to provide for efficient flowing of solutions for the length of the microchannels. In some embodiments, concentrations of Tween (e.g., Tween-20) and BSA are designed to provide activation/wetting of the membranes through the microfluidic channels. In some embodiments, the liquids include between 0.01% and 5% BSA. In some embodiments, the liquids include between 0.01% and 5% Tween.

The antibody in the antibody solution may be polyclonal and/or monoclonal or a mixture of monoclonals of differing antigenic specificities or functional fragments thereof. The antibody may also be one or more primary and/or secondary antibodies.

Referring again to FIG. 1, the light source 106 is configured to irradiate the surface of the membrane 102. Depending on the signal to be detected, the light source 106 may provide light ranging from the ultraviolet range to the far infrared range. Exemplary light sources include lasers and light emitting diodes. In some embodiments, the light source 106 may provide light in multiple wavelength ranges. In some embodiments, the light source 106 is configured to illuminate the membrane 102 by transillumination. In other embodiments, the light source 106 is configured to illuminate the membrane 102 by epi-illumination.

The detector 108 is configured to detect light emitted from the surface of the membrane 102 by the optically detectable proteins 120 and/or the labeled target proteins 122. In some embodiments, detection is achieved by colorimetric, fluorescent, phosphorescent or chemiluminescent detection. In some embodiments, detection is achieved by imaging such as by photography or by electronic detectors. Exemplary electronic detectors include photodiodes, charge-coupled device (CCD) detectors, or complementary metal-oxide semiconductor (CMOS) detectors.

The analog signal from the detector 108 is digitized by an analog-to-digital converter 110. The digitized signal is processed by a microprocessor 112 to obtain at least one value or intensity of detected light that is store in memory 114 and/or displayed on an optional display 116.

By using appropriate electronics and software, the system 100 can be programmed to know the identity and location of optically detectable proteins 120 and target proteins 122 on the surface of the membrane 102.

Methods

Figure 6:
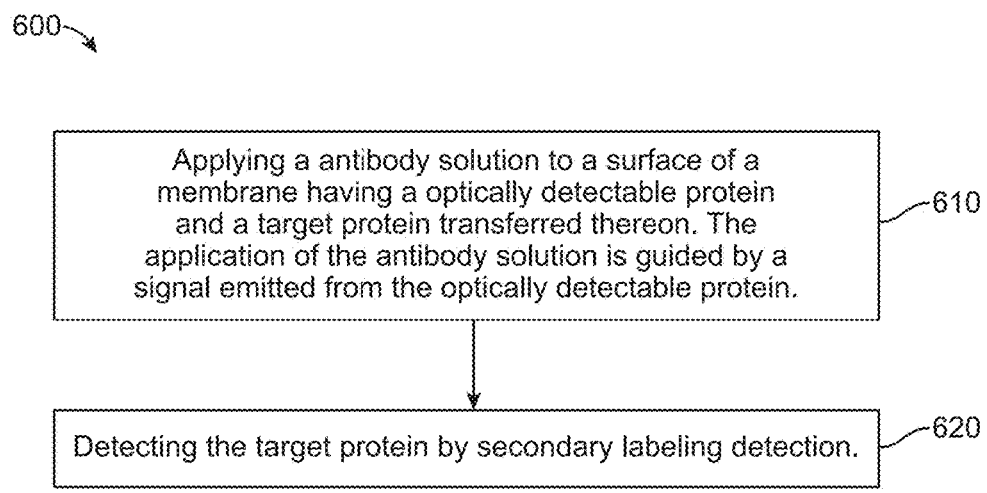
FIG. 6 is a flow chart showing a method of applying an antibody solution to a surface of a membrane having optically detectable transferred proteins using the system of FIG. 1 according to an embodiment of the invention.

Referring to FIG. 6, a method 600 for immunoblotting that uses the aforementioned system 100 will now be described.

In exemplary step 610, an antibody solution is applied to a surface of a wet membrane 102 having an optically detectable protein and a target protein transferred thereon, wherein the application of the antibody solution is guided by a signal emitted from the optically detectable protein. In some embodiments, a map of the transferred optically detectable proteins (e.g., a map of the fluorescent protein bands and lanes) is computer generated and is superimposed over the membrane 102 to guide the application of a line or spot of one or more primary and/or secondary antibody-containing solutions to the entire lane or portions of the lane. In an embodiment, two fluorescent protein bands spanning a molecular weight region that includes the target protein may be used to guide the application of primary and/or secondary antibody solutions. In some embodiments, 30 kilodalton and 50 kilodalton fluorescent protein bands may be used to guide the application of antibody solutions to a target protein having a molecular weight of 40 kilodaltons.

In an embodiment, the optically detectable proteins 120 are haloalkylated proteins and haloalkylated tryptophan fluorescence is used to control the application of one or more antibody solutions to the surface of the membrane 102. In some embodiments, the haloalkylated tryptophan-containing protein has a known content (or number) of haloalkylated tryptophan residues which give a measurable fluorescence when the protein is irradiated with UV light. In some embodiments, the haloalkylated tryptophan-containing transferred protein is a target protein.

In another embodiment, the optically detectable proteins 120 may be proteins labeled with a fluorescent dye or a colorimetric stain as described previously.

In an embodiment, one or more antibody solutions are applied to the surface of the membrane 102 with one or more microfluidic probes 200. In another embodiment, the microfluidic probe 400 (FIG. 4) having more than one microchannel is used to apply one or more antibody solutions to the surface of the membrane 102. In yet another embodiment, probe array 500 (FIG. 5) is used to apply one or more antibody solutions to the surface of the membrane 102. In some embodiments, after application, an antibody solution may be allowed to incubate with material on the surface of the membrane 102 for about 5 minutes to 60 minutes.

The method 600 may further include a wash step after the antibody solution is applied to remove unbound antibody. In some embodiments, the wash step is concurrent with the application of antibody step. In some embodiments, a blocking solution is applied to the surface of the membrane 102 prior to applying the antibody solution.

In exemplary step 620, the target protein is detected by, for example, secondary labeling detection. In some embodiments, the antibody binding to the target protein is visualized and/or detected through the use of a detectable moieties and/or labels. The detectable moieties may be detected by detector 108 or by a different detector. Suitable labels and/or moieties are detected by spectroscopic, photochemical, biochemical, immunochemical, electrical, optical or chemical techniques. In some embodiments the primary and/or secondary antibodies are linked to a detection moiety that is detectable by spectrophotometric, photochemical, biochemical, immunochemical, electrical, optical or chemical techniques. In some embodiments, detection is performed enzymatically using, for example horseradish peroxidase or alkaline phosphatase. In some embodiments, the detection moiety is a fluorophore including, but not limited to, Alexa dyes (e.g., Alexa 350, Alexa 430, etc.), AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine and/or Texas Red. In some embodiments, the detection moiety is an infrared light-absorbing dye including, but not limited to, IRDye 800CW, IRDye 680LT, IRDye, 700DX, and/or IRDye 680.

Figure 7:
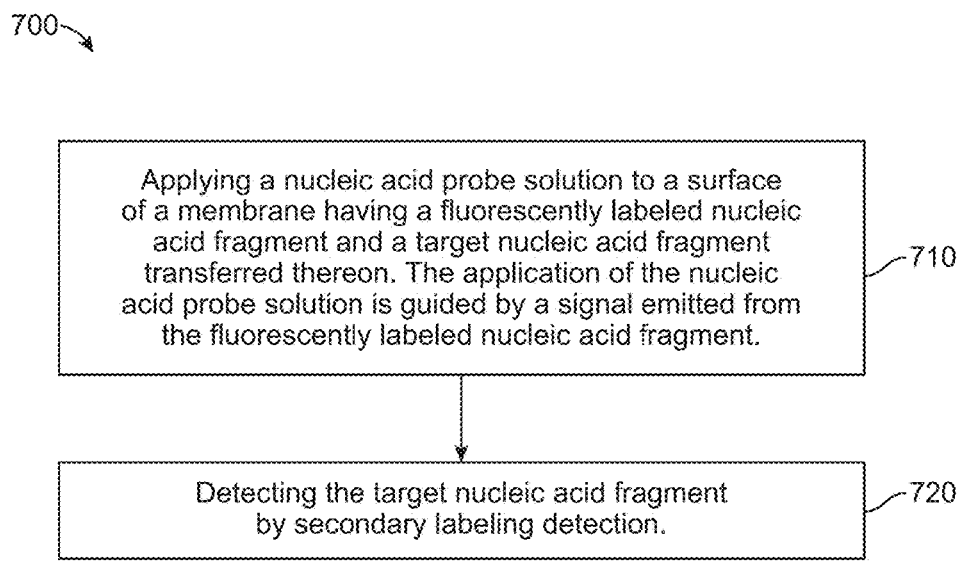
FIG. 7 is a flow chart showing a method of applying a nucleic acid probe solution to a surface of a membrane having fluorescently labeled nucleic acid fragments according to an embodiment of the invention.

Referring to FIG. 7, a method 700 for blotting (i.e., Southern or Northern blotting) that uses the aforementioned system 100 will now be described.

In exemplary step 700, a nucleic acid probe solution is applied to a surface of a wet membrane having a fluorescently-labeled (e.g., ethidium bromide-labeled) nucleic acid fragment and a target nucleic acid fragment transferred thereon, wherein the application of the nucleic acid probe solution is guided by a signal emitted from the fluorescently-labeled nucleic acid fragment. In some embodiments, a map of the transferred fluorescently-labeled nucleic acid fragments (e.g., a map of the fluorescently-labeled nucleic acid fragment bands and lanes) is computer generated and is superimposed over the membrane 102 to guide the application of a line or spot of one or more nucleic acid probe solutions to the entire lane or portions of the lane. In an embodiment, two fluorescently-labeled nucleic acid fragments spanning a molecular weight region that includes the target nucleic acid fragment may be used to guide the application of nucleic acid probe solutions. In some embodiments, 0.2 kilobase and 1.2 kilobase fluorescently-labeled nucleic acid fragment bands may be used to guide the application of nucleic acid probe solutions to a target nucleic acid fragment having a molecular weight of 0.8 kilobases.

In an embodiment, one or more nucleic acid probe solutions are applied to the surface of the membrane 702 with one or more microfluidic probes 200. In another embodiment, the microfluidic probe 400 (FIG. 4) having more than one microchannel is used to apply one or more nucleic acid probe solutions to the surface of the membrane 102. In yet another embodiment, probe array 500 (FIG. 5) is used to apply one or more nucleic acid probe solutions to the surface of the membrane 102. In some embodiments, after application, a nucleic acid probe solution may be allowed to incubate with material on the surface of the membrane 102 for about 1 minute to 60 minutes.

The method 700 may further include a wash step after the nucleic acid probe solution is applied to remove unbound material. In some embodiments, the wash step is concurrent with the application of nucleic acid probe solution step. In some embodiments, a blocking solution is applied to the surface of the membrane 102 prior to applying the nucleic acid probe solution.

In exemplary step 720, the target nucleic acid is detected by, for example, secondary labeling detection. In some embodiments, the nucleic acid probe binding to the target nucleic acid is visualized and/or detected through the use of detectable moieties and/or labels. The detectable moieties may be detected by detector 108 or by a different detector. Suitable labels and/or moieties are detected by isotopic, spectroscopic, photochemical, biochemical, electrical, optical or chemical techniques. In some embodiments the nucleic acid probe is linked to a detection moiety that is detectable by isotopic, spectrophotometric, photochemical, biochemical, electrical, optical or chemical techniques. In some embodiments, detection is performed enzymatically using, for example horseradish peroxidase or alkaline phosphatase. In some embodiments, the detection moiety is a fluorophore including, but not limited to, biotin, fluorescein, DNP, fucose and/or Texas Red.

Computer Implemented Methods and Systems

Any of the methods described herein may be totally or partially performed with a computer system including one or more processors, which can be configured to perform the steps of the methods. Thus, embodiments can be directed to computer systems configured to perform the steps of any of the methods described herein, potentially with different components performing a respective step or a respective group of steps. Although presented as numbered or ordered steps, steps of the methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In some embodiments, the computer implemented method is implemented by a computer system that is in electronic communication with an image scanner that is capable of detecting the optically detectable protein (e.g., protein bands) in a membrane or in an image of a membrane. The computer implemented method can detect labeled protein bands and can use the detected protein bands to guide movement of the dispenser as one or more antibody solutions are applied to the surface of the membrane.

The disclosure further provides a computer product that is capable of performing any one of or all of the steps of the methods described herein. Thus, in some embodiments, the computer product comprises a non-transitory computer readable medium storing a plurality of instructions for controlling a processor to perform an operation of one or more of the method steps described herein.

Figure 8:
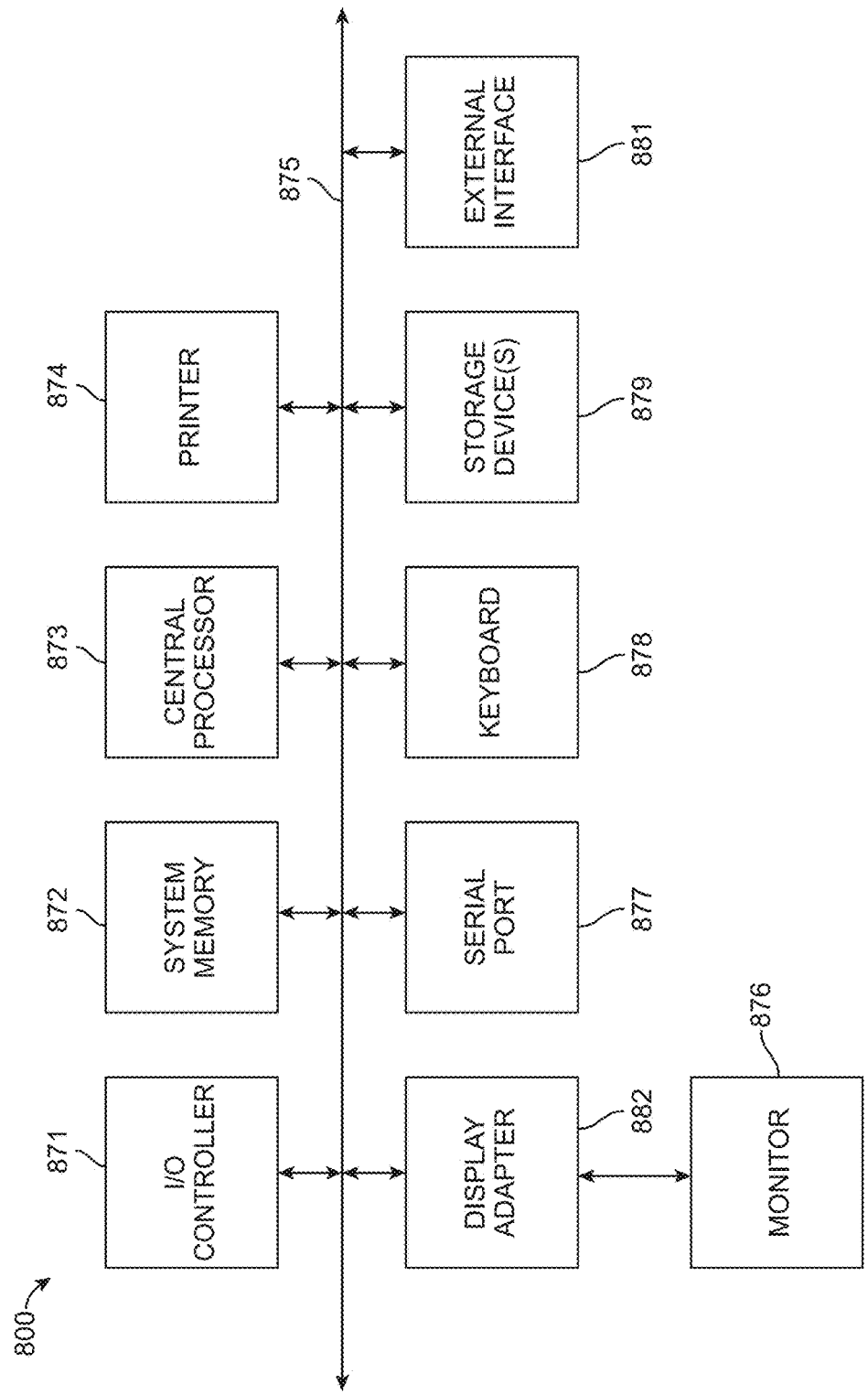
FIG. 8 shows a block diagram of an example computer system usable with the systems and methods according to embodiments of the invention.

FIG. 8 shows a block diagram of an example computer system 800 usable with system and methods according to embodiments of the present disclosure.

Any of the computer systems mentioned herein may utilize any suitable number of subsystems. Examples of such subsystems are shown in FIG. 8 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 8 are interconnected via a system bus 875. Additional subsystems such as a printer 874, a keyboard 878, a storage device(s) 879, a monitor 876, which is coupled to a display adapter 882, and others are shown. Peripherals and input/output (I/O) devices, which couple to I/O controller 871, can be connected to the computer system by any number of means known in the art, such as a serial port 877. For example, the serial port 877 or an external interface 881 (e.g. Ethernet, Wi-Fi, etc.) can be used to connect the computer system 800 to a wide area network such as the Internet, a mouse input device, or a scanner. The interconnection via the system bus 875 allows the central processor 873 to communicate with each subsystem and to control the execution of instructions from the system memory 872 or the storage device(s) 879 (e.g., a fixed disk, such as a hard drive or optical disk), as well as the exchange of information between subsystems. The system memory 872 and/or the storage device(s) 879 may embody a computer readable medium. Any of the data mentioned herein can be output from one component to another component and can be output to the user.

A computer system can include a plurality of the same components or subsystems, e.g., connected together by the external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that the embodiments described above can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Additional Disclosure and Claimable Subject Matter

Item 1. A method of immunoblotting comprising:
applying an antibody solution to a surface of a membrane having an optically detectable protein and a target protein transferred thereon, wherein the application of the antibody solution is guided by a signal emitted from the optically detectable protein; and
detecting the target protein.

Item 2. The method of Item 1, further comprises a washing step in which unbound material is removed from the membrane.

Item 3. The method of Item 2, wherein the applying an antibody solution step is concurrent with the washing step.

Item 4. The method of any one of previous Items 1 to 3, wherein the applying an antibody solution step comprises dispensing a microfluidic volume of the antibody solution.

Item 5. The method of any one of previous Items 1 to 3, wherein the applying an antibody solution step comprises dispensing a sub-microfluidic volume of the antibody solution.

Item 6. The method of any one of previous Items 1 to 3, wherein the applying an antibody solution step comprises dispensing the antibody solution with a technique selected from a group consisting of hydrodynamic flow confinement, ink jet printing, spray deposition, microspotting and microcontact printing.

Item 7. The method of Item 6, wherein the applying an antibody solution step comprises dispensing the antibody solution with a microfluidic probe.

Item 8. The method of Item 7, wherein the microfluidic probe comprises multiple microchannels.

Item 9. The method of Item 7 or 8, wherein the microfluidic probe is an array of microfluidic probes.

Item 10. The method of any one of previous Items 1 to 9, wherein the applying an antibody solution step comprises dispensing an antibody solution in at least one discreet path on the surface of the membrane.

Item 11. The method of Item 10, wherein the path spans the length of one or more lanes of protein bands.

Item 12. The method of Item 10, wherein the path is from 25 nanometers to 500 micrometers wide.

Item 13. The method of any one of previous Items 1 to 9, wherein the applying an antibody solution step comprises dispensing two antibody solutions each in a discreet path on a lane on the surface of the membrane.

Item 14. The method of any one of previous Items 1 to 9, wherein the applying an antibody solution step comprises dispensing an antibody solution in at least one discreet spot.

Item 15. The method of any one of previous Items 1 to 9, wherein the applying an antibody solution step comprises dispensing a primary antibody solution and a secondary antibody solution.

Item 16. The method of any one of previous Items 1 to 9, wherein the membrane comprises a material selected from the group consisting of polyvinylidene fluoride, nitrocellulose, nylon and polysulfone.

Item 17. The method of any one of previous Items 1 to 16, wherein the optically labeled protein transferred onto the membrane is labeled with a substance selected from the group consisting of a fluorescent dye, a colorimetric dye and haloalkane.

Item 18. The method of any one of Items 1 to 17, further comprising applying a blocking solution to the surface of the membrane prior to applying the antibody solution.

Item 19. An immunoblotting system comprising:
a membrane having an optically detectable protein transferred thereon;
a dispenser configured to dispense an antibody solution;
a detector configured to detect the optically detectable protein;
a processor; and
a memory comprising a data storage unit for storing instructions that are executable by the processor and that configure the system to dispense the antibody solution in accordance with the optically detectable protein detected by the detector.

Item 20. The immunoblotting system of Item 19, wherein the detector is further configured to detect a target protein.

Item 21. The immunoblotting system of Item 19 or 20, further comprising a second detector configured to detect a target protein.

Item 22. The immunoblotting system of any one of previous Items 19 to 21, wherein the dispenser is selected from a group consisting of a hydrodynamic flow confinement dispenser, an ink jet printer, a spray deposition dispenser, a microspotter and a microcontact printer.

Item 23. The immunoblotting system of any one of previous Items 19 to 22, wherein the dispenser is a microfluidic probe.

Item 24. The immunoblotting system of Item 23, wherein the microfluidic probe comprises multiple microchannels.

Item 25. The immunoblotting system of Item 23, wherein the microfluidic probe is an array of microfluidic probes.

Item 26. A method of immunoblotting comprising:
applying an antibody solution to a surface of a membrane having a haloalkylated tryptophan-containing protein and a target protein transferred thereon, wherein the application of the antibody solution is guided by a fluorescence of the haloalkylated tryptophan-containing protein; and
detecting the target protein.

Item 27. An immunoblotting system comprising:
a membrane having a transferred haloalkylated tryptophan-containing protein;
a dispenser configured to dispense an antibody solution;
a detector configured to detect the haloalkylated tryptophan-containing protein;
a processor; and
a memory comprising a data storage unit for storing instructions that are executable by the processor and that configure the system to dispense the antibody solution in accordance with the transferred haloalkylated tryptophan-containing protein detected by the detector.

Item 28. A method of blotting comprising:
applying a nucleic acid probe to a surface of a membrane having a fluorescently-labeled nucleic acid fragment and a target nucleic acid fragment transferred thereon, wherein the application of the nucleic acid probe is guided by an signal emitted from the fluorescently-labeled nucleic acid fragment; and
detecting the target nucleic acid fragment.

Item 29. The method of Item 28, further comprises a washing step in which unbound material is removed from the membrane.

Item 30. The method of Item 29, wherein the applying a probe step is concurrent with the washing step.

Item 31. The method of any one of previous Items 28 to 30, wherein the applying a nucleic acid probe step comprises dispensing a microfluidic volume of the probe.

Item 32. The method of any one of previous Items 28 to 30, wherein the applying a nucleic acid probe step comprises dispensing a sub-microfluidic volume of the probe.

Item 33. The method of any one of previous Items 28 to 32, wherein the applying a nucleic acid probe step comprises dispensing the nucleic acid probe with a technique selected from a group consisting of hydrodynamic flow confinement, ink jet printing, spray deposition, microspotting and microcontact printing.

Item 34. The method of any one of previous Items 28 to 33, wherein the applying a nucleic acid probe step comprises dispensing the nucleic acid probe with a microfluidic probe.

Item 35. The method of Item 34, wherein the microfluidic probe comprises multiple microchannels.

Item 36. The method of Item 34, wherein the microfluidic probe is an array of microfluidic probes.

Item 37. The method of any one of previous Items 28 to 36, wherein the applying a nucleic acid probe step comprises dispensing the nucleic acid probe in at least one discreet path on the surface of the membrane.

Item 38. The method of Item 37, wherein the path spans the length of one or more lanes of protein bands.

Item 39. The method of Item 37, wherein the path is from 25 nanometers to 500 micrometers wide.

Item 40. The method of claim 28, wherein the applying a nucleic acid probe step comprises dispensing two nucleic acid probes each in a discreet path on a lane on the surface of the membrane.

Item 41. The method of any one of previous Items 28 to 36, wherein the applying a nucleic acid probe step comprises dispensing the nucleic acid probe in at least one discreet spot.

Item 42. The method of any one of previous Items 28 to 41, wherein the membrane comprises a material selected from the group consisting of polyvinylidene fluoride, nitrocellulose, nylon and polysulfone.

Item 43. The method of any one of previous Items 28 to 42, wherein the fluorescently-labeled nucleic acid fragment transferred onto the membrane is labeled with ethidium bromide.

Item 44. The method of any one of previous Items 28 to 43, further comprising applying a blocking solution to the surface of the membrane prior to applying the nucleic acid probe.

Item 45. An blotting system comprising:
a membrane having a fluorescently-labeled nucleic acid fragment transferred thereon;
a dispenser configured to dispense a nucleic acid probe;
a detector configured to detect the fluorescently-labeled nucleic acid fragment;
a processor; and
a memory comprising a data storage unit for storing instructions that are executable by the processor and that configure the system to dispense the nucleic acid probe in accordance with the fluorescently-labeled nucleic acid fragment detected by the detector.

Item 46. The blotting system of Item 45, wherein the detector is further configured to detect a target nucleic acid fragment.

Item 47. The blotting system of Item 45 or 46, further comprising a second detector configured to detect a target nucleic acid fragment.

Item 48. The blotting system of any one of previous Items 45 to 47, wherein the dispenser is selected from a group consisting of a hydrodynamic flow confinement dispenser, an ink jet printer, a spray deposition dispenser, a microspotter and a microcontact printer.

Item 49. The blotting system of any one of previous Items 45 to 48, wherein the dispenser is a microfluidic probe.

Item 50. The blotting system of Item 49, wherein the microfluidic probe comprises multiple microchannels.

Item 51. The blotting system of Item 49 or 50, wherein the microfluidic probe is an array of microfluidic probes.

EXAMPLES

Example 1: Immunoblotting Using a Microfluidic Probe

The following describes one proposed method for multiplex western blotting using the microfluidic probes to detect four different proteins in brain tissues on a single blot.

The first step of the method involves protein extraction from brain tissues of 12 age matched normal or Alzheimer disease mice using a lysis buffer (50 mM Tris-HCl pH 8.0, 150 mM NaCl, 1% NP-40, 0.5% sodium deoxycholate, 0.1% SDS, supplemented with phosphatase and protease inhibitors). Take 20 µg of each sample, add an equal volume of 2× Laemmli Sample Buffer (4% SDS, 10% 2-mercaptoethanol, 20% glycerol, 0.004% bromophenol blue, 125 mM Tris-HCl, pH 6.8). Heat each cell lysate in sample buffer at 95° C. for 5 min. Load the protein samples and appropriate protein markers to a 4-15% Bio-Rad TGX Stain Free Criterion™ gel 12+2 well. Run the gel for ~60 min at 100 V using the Tris-Glycine running buffer (2.5 mM Tris, 190 mM glycine, 0.1% SDS, pH 8.3).

When the electrophoresis step is completed, remove the gel cassette from the Criterion™ cell and remove the gel from the cassette. Place the gel on the UV sample tray of the Bio-Rad ChemiDoc™ Touch imager. Turn on the UV light to activate the haloalkylated proteins in the gel for 1 min so that the protein bands can be fluorescently detected after electroblotting. Remove the gel from the tray and assemble a transfer sandwich with a low fluorescent PVDF membrane. Place the sandwich in a Bio-Rad Trans-Blot Turbo system and transfer for 7 min at 25V.

After protein transfer is completed, the low fluorescent PVDF membrane blot is placed in the blocking buffer (3% bovine serum albumin, 20 mM Iris pH 7.5, 150 mM NaCl, 0.1% Tween 20) in a container and mounted to a X-Y-Z platform in the microfluidic probe immunoblotting system. A fluorescent image of the blot is taken to locate the protein lanes and bands. The computer uses the fluorescent image of the protein lanes and bands to create a map that is superimposed over the membrane to automatically drive the microfluidic probe to dispense 4 different antibody solutions (each using a different microfluidic probe) onto each sample lane. Each antibody solution is dispensed in a line 25 nanometers-200 micrometers wide. The antibody solutions are prepared in the following way: 1) Tau (Tau46) mouse monoclonal antibody #4019 (Cell Signaling Technology) diluted 1:50 in the ReadyTector® all-in-one buffer (CONDOR BioScience); 2) Phospho-Tau (Ser396) (PHF13) mouse monoclonal antibody #9632 (Cell Signaling Technology) diluted 1:50 in the ReadyTector® all-in-one buffer; 3) α-Synuclein (Syn204) Mouse mAb #2647 (Cell Signaling Technology) diluted 1:50 in the ReadyTector® all-in-one buffer; 4) APP/β-Amyloid (NAB228) Mouse mAb #2450 (Cell Signaling Technology) diluted 1:50 in the ReadyTector all-in-one buffer. The ReadyTector® all-in-one buffer contains the HRP conjugated Goat anti-mouse antibodies. While each of the four antibody solutions is dispensed in each of the 12 lanes of the gel, the microprobe is used to wash the blot by dispensing TBS buffer (20 mM Tris pH 7.5, 150 mM NaCl).

The blot is next removed from the microfluidic probe immunostaining system and rinsed in TBS buffer one more time to remove the excessive antibody and bovine serum albumin in the blocking buffer. The blot is then incubated for 5 min with premixed Bio-Rad Clarity ECL substrate. The resulting blot is placed on the Chemi tray of a ChemiDoc™ Touch system to acquire a chemiluminescence image. The intensities of the target protein bands are measured using the Bio-Rad Image Lab software and normalized against the total loading control measured on the stain free blot image.

Example 2: Immunoblotting Using a Traditional Method

The following describes a typical conventional western blot method to detect four different proteins in brain tissues on a single blot.

The first step of a conventional western blot method involves protein extraction from brain tissues of 12 age matched normal or Alzheimer disease mice using a lysis buffer (50 mM Tris-HCl pH 8.0, 150 mM NaCl, 1% NP-40, 0.5% sodium deoxycholate, 0.1% SDS, supplemented with phosphatase and protease inhibitors). Take 20 μg of each sample, add an equal volume of 2× Laemmli Sample Buffer (4% SDS, 10% 2-mercaptoethanol, 20% glycerol, 0.004% bromophenol blue, 125 mM Tris-HCl, pH 6.8). Heat each cell lysate in sample buffer at 95° C. for 5 min. Load the protein samples and appropriate protein markers to a 4-15% Bio-Rad TGX Critrion™ gel 12+2 well. Run the gel for ~60 min at 100 V using the Tris-Glycine running buffer (25 mM Tris, 190 mM glycine, 0.1% SDS, pH 8.3).

After the electrophoresis is completed, place the gel in 1× transfer buffer (25 mM Tris, 190 mM glycine, 20% methanol) for 10-15 min. Assemble the transfer sandwich using a regular PVDF membrane and make sure no air bubbles are trapped in the sandwich. The blot should be on the anode and the gel on the cathode. Place the sandwich cassette in a transfer tank and place an ice block in the tank. Transfer overnight in a cold room at a constant current of 10 mA.

When protein transfer is completed, place the PVDF membrane blot in 3% BSA in TBST (20 mM Tris pH 7.5, 150 mM NaCl, 0.1% Tween 20) at room temperature for 1 hr. Incubate the blot overnight in 10 ml of Tau (Tau46) mouse monoclonal antibody solution at 4° C. The antibody is diluted 1:1000 in the blocking buffer. Rinse the blot 5 times for 5 min with TBST before applying the HRP-conjugated goat anti mouse antibody solution for 1 hr at room temperature. The blot is again rinsed 5 times for 5 min with TBST.

When the antibody incubation step is completed, apply the chemiluminescent substrate to the blot. Capture the chemiluminescent signals using the Bio-Rad ChemiDoc™ Touch system. Use image analysis software to read the band intensity of the target proteins.

To detect the second protein target on the membrane, the blot is stripped in the stripping buffer (20 ml 10% SDS, 12.5 ml 0.5 M Tris HCl, 67.5 ml ultrapure water, 0.8 ml β-mercaptoethanol) at 50° C. for up to 45 min with agitation. The membrane is then rinse in water for 1 hr. Repeat the antibody incubation and imaging steps described above to apply Phospho-Tau (Ser396) (PHF13) mouse monoclonal antibody to detect the phosphorylated tau proteins.

Strip and reprobe the blot three more times to detect the following targets: α-Synuclein using the mouse mAb #2647 (1:1000, Cell Signaling Technology); APP/β-Amyloid using the mouse mAb #2450 (1:1000, Cell Signaling Technology), and the housekeeping loading control protein β-Actin using the Mouse mAb #3700 (1:1000, Cell Signaling Technology). The intensities of the proteins of interest are measured off the chemiluminescent blot images using the Bio-Rad Image Lab software and normalized against the housekeeping protein loading control β-Actin.

Example 3: Comparison of Traditional and Microfluidic Probe-Based Immunoblotting The microfluidic probe-based immunoblotting have the following major benefits/difference over the conventional western blotting:
1) Automated antibody probing steps: The microfluidic probe immunoblotting system automatically dispenses antibody solution to each sample lane and replaces more than 10 steps of manual buffer changing steps in the conventional method. The hands-free procedure frees up the research scientists from the long protocol and allows them to focus on other projects. It increases lab productivity.
2) Reproducibility: The automated antibody probing procedure offers precision in space, time and concentration in antibody dispensing, resulting in better control of the dynamics of antibody-antigen interaction. This translates into more reproducible data compared to the conventional protocol.
3) Multiplex without stripping and reprobing: The microfluidic probe delivers different antibodies in discreet paths on each sample lane. The antibodies against different targets do not mix with each other, eliminating the crossreactivity issues associated with conventional multiplex immunoassays and the need for stripping and reprobing.
4) Saves antibody: Microfluidic probe dispenses antibodies in a 25 nanometer to 200 micrometer wide path on each sample lane instead of to the whole membrane blot. This could potentially reduce antibody consumption for each experiment.

Example 4: Immunoblotting Using a Microfluidic Probe and a Model Target Antigen

This example illustrates the use of an optically detectable protein transferred to a Western blot membrane to guide the application of a primary antibody solution to a surface of a blotting membrane having a model target antigen (e.g., a target protein) transferred thereon. The application of the primary antibody by a microfluidic probe is guided by optically detectable protein standards in a lane adjacent to the target antigen.

For sodium dodecyl sulfate polyacrylamide gel electrophoresis (SDS-PAGE), a Bio-Rad 4-20% Mini-PROTEAN® TGX Protein Gel (catalog #4561094) with 10 wells was used. A stock solution of the human serum albumin (hSA) protein (10 mg/ml Rockland cat#009-0133) was used as the model target antigen. The hSA was diluted 7500 times in buffer. The buffer comprised standard Laemmli sample buffer (Bio-Rad cat#161-0747) with 355 mM 2-mercaptoethanol (Bio-rad cat#161-0710) and phosphate buffered saline (PBS). The diluted hSA sample was pre-treated by heating to 95° C. for 10 min. For the gel, 15 ul of the heated hSA sample was loaded into even lanes (total amount of 20 ng of hSA) while the odd lanes were loaded with a molecular weight ladder (Precision Plus Protein™ Dual Color Standards, Bio-Rad cat#1610394). Electrophoretic separation was performed for about 40 min at 200 V with the Bio-Rad Mini-PROTEAN® Tetra Cell using Tris-Glycine running buffer (25 mM Tris, 109 mM glycine, 0.1% SDS, pH 8.3). After electrophoretic separation, the gel was washed in distilled water.

After gel electrophoresis, the gel was removed from the gel cassette and the protein bands were transferred to a low fluorescence PVDF membrane (from the Bio-Rad Trans-Blot® Turbo™ RTA Mini LF PVDF Transfer Kit, Cat#1704274) using a Bio-Rad Trans-Blot Turbo system and a transfer time of 7 minutes at 25 V. The PVDF membrane had been previously activated by treating the membrane with 99% methanol. After protein transfer, the PVDF membrane was immersed in a blocking solution of non-fat dry milk blocker (Bio-Rad cat#170-6404), 5% TBS buffer (cat#170-6435) with 0.1% Tween 20 (or TBST buffer) for 1 hour under mild shaking.

Figure 9A:
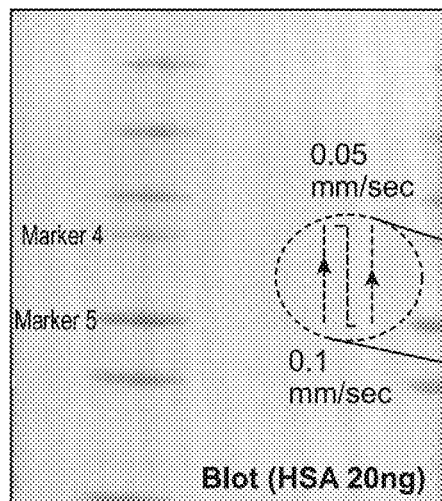
FIGS. 9A-9C show immunoblotting results using a microfluidic probe and a model target antigen (e.g., human serum antigen, hSA).

As illustrated in FIG. 9A, the prestained protein standards in the lanes flanking the lane with hSA were used to visually determine where to apply 250 ug/ml primary antibody (rabbit anti-hSA polyclonal diluted 1:4 with blocking solution; Rockland cat#600-401-033) to the blot membrane with the microfluidic probe (IBM Research, Zurich). The primary antibody was applied in a line perpendicular to the estimated location of the hSA band in the region between Marker 4 and Marker 5. The height of the microfluidic probe above the membrane was 80 micrometers and the velocity of the processing liquid containing the dilute primary antibody was 0.1 millimeters/second or 0.05 millimeters/second. The width of the line of primary antibody dispensed was about 50 nanometers to about 200 micrometers, depending on the velocity of the processing liquid. The membrane was immersed in blocking solution (i.e., the immersion liquid) during application of the primary antibody. As primary antibody was injected from an injection channel into the immersion liquid and onto the surface of the blotting membrane in the lane containing the hSA band, primary antibody mixed with immersion liquid was aspirated back into an aspiration channel such that application of primary antibody and subsequent removal of unbound primary antibody were concurrent.

Figure 9B:
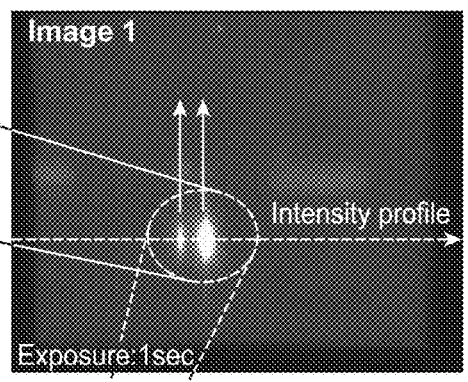
Figure 9C:
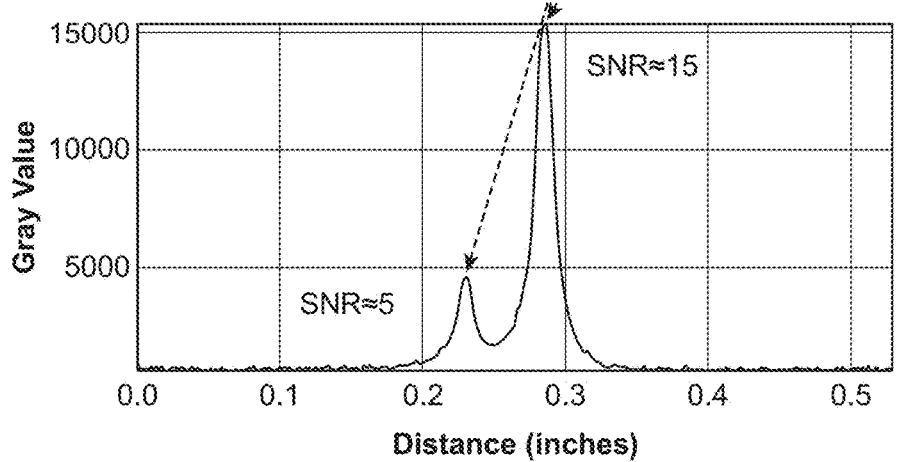

After applying the primary antibody to the hSA band with the microfluidic probe, the blot was washed three times in TBST for 5 minutes each wash (15 minutes in total). The blot was then immersed in a solution of 30 ug/ml secondary antibody (1.5 mg/ml FITC conjugated anti-rabbit mouse polyclonal antibody diluted 1:50 in blocking solution; Jackson cat#111-095-003). The blot was again washed three times in TBST for 5 minutes each wash. As illustrated in FIG. 9B, the hSA band was detected and imaged with a Bio-Rad ChemiDoc™ MP imager using the fluorescein mode (excitation—blue epi light; emission 530/28; exposure time of 1 second). FIG. 9C shows an intensity profile (e.g., relative signal intensity as a function of scan distance) of the bands imaged in FIG. 9B. The intensity profile was determined with ImageJ software (open source).

The results shown in FIGS. 9B and 9C demonstrate that optically detectable proteins (e.g., prestained protein standards) in a lane adjacent to a target antigen on a blotting membrane can be used to guide application of a primary antibody solution to the blotting membrane. The primary antibody was applied only to the portion of the lane Example 5: Immunoblotting Using a Microfluidic Probe and a Model Target Antigen Mixed with Optically Detectable Proteins This example illustrates guiding the application of a primary antibody solution to a surface of a blotting membrane having an optically detectable protein and a target antigen transferred thereon. The application of the primary antibody by a microfluidic probe is guided by optically detectable protein standards, all of which are in the same lane on the blotting membrane.

A Bio-Rad 4-20% Mini-PROTEAN® TGX Stain-Free™ Protein Gel (catalog #4568091) with a 7 cm IPG/prep well was used for SDS-PAGE. A stock solution of hSA protein (10 mg/ml Rockland cat#009-0133) was used as the model target antigen. The hSA was diluted 7500 times in buffer. The buffer comprised standard Laemmli sample buffer (Bio-Rad cat#161-0747) with 355 mM 2-mercaptoethanol (Bio-rad cat#161-0710) and PBS. The diluted hSA sample was pre-treated by heating to 95° C. for 10 min. For the gel, 400 ul of the heated hSA sample was mixed with 30 ul of the molecular weight ladder (Precision Plus Protein™ Dual Color Standards, Bio-Rad cat#1610394) and the mixture was loaded into the well. Electrophoretic separation was performed for about 40 min at 200 V with the Bio-Rad Mini-PROTEAN® Tetra Cell using Tris-Glycine running buffer (25 mM Tris, 109 mM glycine, 0.1% SDS, pH 8.3). After electrophoretic separation, the gel was washed in distilled water.

After gel electrophoresis, the gel was removed from the gel cassette and the protein bands were transferred to a low fluorescence PVDF membrane (from the Bio-Rad Trans-Blot® Turbo™ RTA Mini LF PVDF Transfer Kit, Cat#1704274) using a Bio-Rad Trans-Blot Turbo system and a transfer time of 7 minutes at 25 V. The PVDF membrane had been previously activated by treating the membrane with 99% methanol. After protein transfer, the PVDF membrane was immersed in a blocking solution of non-fat dry milk blocker (Bio-Rad cat#170-6404), 5% TBS buffer (cat#170-6435) with 0.1% Tween 20 (or TBST buffer) for 1 hour under mild shaking.

Figure 10A:
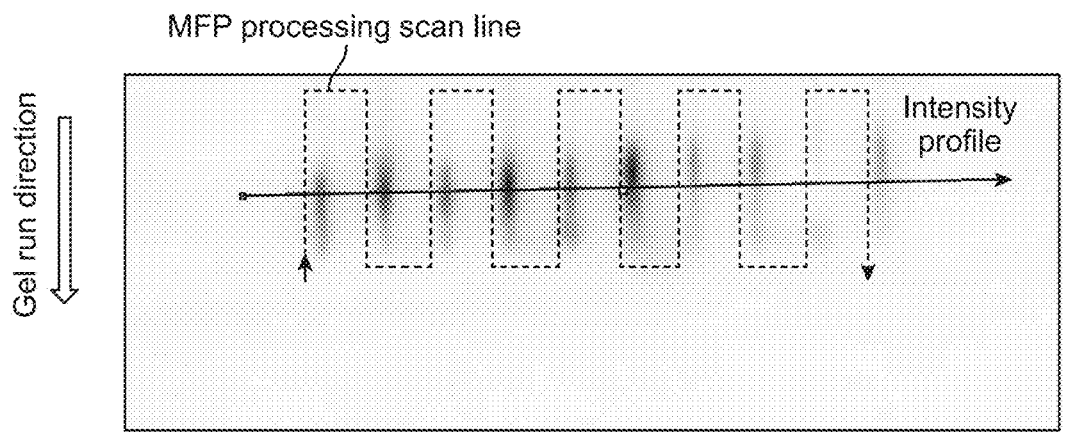
FIGS. 10A and 10B show more immunoblotting results using a microfluidic probe and a model target antigen (e.g., hSA).

The prestained protein standards in the same lane as the hSA were used to visually determine where to apply 250 ug/ml primary antibody (rabbit anti-hSA polyclonal diluted 1:4 with blocking solution; Rockland cat#600-401-033) to the blot membrane with the microfluidic probe (IBM Research, Zurich). The primary antibody was applied in a line perpendicular to the estimated location of the hSA band in the region between Marker 4 and Marker 5. Because the prep well was used to load the mixture of prestained protein standards and the hSA, 7 cm wide bands for the standards and the hSA were obtained such that multiple applications of the primary antibody with the microfluidic probe were performed. In FIG. 10A, the path of the probe is illustrated as scan lines shifted to the left of the actually path of the probe to avoid hiding the signal. The height of the microfluidic probe above the membrane was 80 micrometers and the velocity of the processing liquid containing the dilute primary antibody was 0.05 millimeters/second. The width of the line of primary antibody dispensed was about 200 micrometers. The membrane was immersed in blocking solution (i.e., the immersion liquid) during application of the primary antibody. As primary antibody was injected from an injection channel into the immersion liquid and onto the surface of the blotting membrane in the lane containing the hSA band, primary antibody mixed with immersion liquid was aspirated back into an aspiration channel such that application of primary antibody and subsequent removal of unbound primary antibody were concurrent.

Figure 10B:
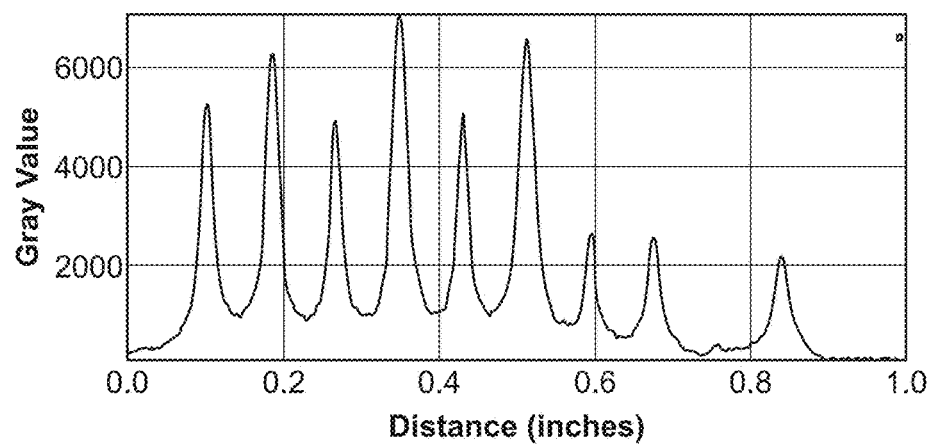

After applying the primary antibody to the hSA band with the microfluidic probe, the blot was washed three times in TBST for 5 minutes each wash (15 minutes in total). The blot was then immersed in a solution of 30 ug/ml secondary antibody (1.5 mg/ml FITC conjugated anti-rabbit mouse polyclonal antibody diluted 1:50 in blocking solution; Jackson cat#111-095-003). The blot was again washed three times in TBST for 5 minutes each wash. As illustrated in FIG. 10A, the hSA band was detected and imaged with a Bio-Rad ChemiDoc™ MP imager using the fluorescein mode (excitation—blue epi light; emission 530/28). FIG. 10B shows an intensity profile of the bands imaged in FIG. 10A. The intensity profile was determined with ImageJ software (open source).

The results in FIGS. 10A and 10B demonstrate that optically detectable proteins (e.g., prestained protein standards) in the same lane as the target antigen on a blotting membrane can be used to guide application of a primary antibody solution to the blotting membrane.

The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method of immunoblotting comprising:
   providing a membrane having an optically detectable protein and a target protein transferred thereon;
   applying an antibody solution to a surface of the membrane, wherein the application of the antibody solution is guided by a signal emitted from the optically detectable protein, and wherein the antibody specifically binds to the target protein; and
   detecting the target protein.

2. The method of claim 1, further comprises a washing step in which unbound material is removed from the membrane.

3. The method of claim 2, wherein the applying an antibody solution step is concurrent with the washing step.

4. The method of claim 1, wherein the applying an antibody solution step comprises dispensing a microfluidic volume of the antibody solution.

5. The method of claim 1, wherein the applying an antibody solution step comprises dispensing a sub-microfluidic volume of the antibody solution.

6. The method of claim 1, wherein the applying an antibody solution step comprises dispensing the antibody solution with a technique selected from a group consisting of hydrodynamic flow confinement, ink jet printing, spray deposition, microspotting and microcontact printing.

7. The method of claim 1, wherein the applying an antibody solution step comprises dispensing the antibody solution with a microfluidic probe.

8. The method of claim 7, wherein the microfluidic probe comprises multiple microchannels.

9. The method of claim 7, wherein the microfluidic probe is an array of microfluidic probes.

10. The method of claim 1, wherein the applying an antibody solution step comprises dispensing an antibody solution in at least one discreet path on the surface of the membrane.

11. The method of claim 10, wherein the path spans the length of one or more lanes of protein bands.

12. The method of claim 10, wherein the path is from 25 nanometers to 500 micrometers wide.

13. The method of claim 1, wherein the applying an antibody solution step comprises dispensing two antibody solutions each in a discreet path on a lane on the surface of the membrane.

14. The method of claim 1, wherein the applying an antibody solution step comprises dispensing an antibody solution in at least one discreet spot.

15. The method of claim 1, wherein the applying an antibody solution step comprises dispensing a primary antibody solution and a secondary antibody solution.

16. The method of claim 1, wherein the membrane comprises a material selected from the group consisting of polyvinylidene fluoride, nitrocellulose, nylon and polysulfone.

17. The method of claim 1, wherein the optically labeled protein transferred onto the membrane is labeled with a substance selected from the group consisting of a fluorescent dye, a colorimetric dye and haloalkane.

18. The method of claim 1, further comprising applying a blocking solution to the surface of the membrane prior to applying the antibody solution.

* * * * *